US00PP09105P

United States Patent [19]

VandenBerg

[11] Patent Number: Plant 9,105

[45] Date of Patent: Apr. 11, 1995

[54] CHRYSANTHEMUM PLANT NAMED AKRON

[75] Inventor: Cornelis P. VandenBerg, Salinas, Calif.

[73] Assignee: Yoder Brothers, Inc., Barberton, Ohio

[21] Appl. No.: 280,527

[22] Filed: Jul. 26, 1994

[51] Int. Cl.[6] ..... A01H 5/00

[52] U.S. Cl. ..... Plt./74.1

[58] Field of Search ..... Plt. 74.1, 82.5

*Primary Examiner*—Howard J. Locker

*Attorney, Agent, or Firm*—Foley & Lardner

[57] ABSTRACT

A Chrysanthemum plant named Akron particularly characterized by its flat capitulum form; daisy capitulum type; red-purple ray floret color; diameter across face of capitulum of 64 to 76 mm when fully opened, when grown as a pinched spray pot mum; photoperiodic flowering response to short days of 50 to 56 days; plant height with 14 to 16 long days after sticking unrooted cuttings, and with one application of 2500 ppm B-9 SP, ranging from 18 to 30 cm when grown as a pinched pot mum with four cuttings in a 15 cm pot; branching pattern is spreading and prolific, each plant having 4 to 6 laterals after pinch; and recommended as spray pot mum.

3 Drawing Sheets

The present invention comprises a new and distinct cultivar of Chrysanthemum, botanically known as *Dendranthema grandiflora,* and referred to by the cultivar name Akron.

Akron, identified as 4660 (91-413005), was originated from a cross made by Cornelis P. VandenBerg in a controlled breeding program in Salinas, Calif. in 1991.

The female parent of Akron was an unnnamed seedling identified as 6762 (86-413002) and described as a pot spray mum with a flat capitulum form; anemone capitulum type; dark purple ray floret color; diameter across face of capitulum of 54 to 64 mm when grown as a spray pot mum; flowering response to short days in Salinas, Calf. of 51 to 60 days; plant height of 20 to 28 cm when grown with 15 to 16 long days after sticking unrooted cuttings prior to start of short days and 1 to 2 applications of 2500 ppm B-9 SP; and a branching pattern of 3 to 5 laterals developing after pinch. The female parent was discarded from all programs on May 4, 1993.

The male parent of Akron was the cultivar identified as Lucido, disclosed in U.S. Plant Pat. No. 6,586, and described as a pot spray mum with flat capitulum form; daisy capitulum type; red ray floret color; diameter across face of capitulum of 70 to 83 mm when grown as a spray pot mum; flowering response to short days in Salinas, Calif. of 56 to 60 days; plant height of 23 to 30 cm when grown with 15 to 16 long days after sticking unrooted cuttings prior to start of short days and 1 to 2 applications of 2500 ppm B-9 SP; and a branching pattern of 5 laterals developing after pinch. The ranges of measurements of Lucido are somewhat greater than the measurements disclosed in U.S. Plant Pat. No. 6,586 Lucido. This is based on continuing flowering trials of Lucido.

Akron was discovered and selected as one flowering plant within the progeny of the stated cross by Cornelis P. VandenBerg in January 1992, in a controlled environment in Salinas, Calif.

The first act of asexual reproduction of Akron was accomplished when vegetative cuttings were taken from the initial selection in March 1992 in a controlled environment in Salinas, Calif., by technicians working under supervision of Cornelis P. VandenBerg.

Horticultural examination of controlled flowerings of successive plantings has shown that the unique combination of characteristics as herein disclosed for Akron are firmly fixed and are retained through successive generations of asexual reproduction.

Akron has not been observed under all possible environmental conditions. The phenotype may vary significantly with variations in environment such as temperature, light itensity and daylength, without, however, any variance in genotype.

The following observations, measurements and comparisons describe plants grown in Salinas, Calif. under greenhouse conditions which approximate those generally used in commercial greenhouse practice.

The following traits have been repeatedly observed and are determined to be basic characteristics of Akron, which, in combination, distinguish this Chrysanthemum as a new and distinct cultivar:

1. Flat capitulum form.
2. Daisy capitulum type.
3. Red-purple ray floret color.
4. Diameter across face of capitulum of 64 to 76 mm when fully opened, when grown as a pinched spray pot mum.
5. Photoperiodic flowering response to short days of 50 to 56 days.
6. Plant height, with 14 to 16 long days after sticking unrooted cuttings, and with one application of 2500 ppm B-9 SP, ranges from 18 to 30 cm when grown as a pinched pot mum with four cuttings in a 15 cm pot.
7. Branching pattern is spreading and prolific, each plant having 4 to 6 laterals after pinch.
8. Recommended as spray pot mum.

The accompanying photographic drawings show typical inflorescence and leaf characteristics of Akron, with the colors being as nearly true as possible with illustrations of this type.

Sheet 1 is a color photograph of Akron grown as a pinched spray pot mum with four cuttings in a 15 cm pot.

Sheet 2 is a black and white photograph of three views of the inflorescence of Akron.

Sheet 3 is a black and white photograph showing the upper and under sides of the leaves of Akron at 3 stages of development (mature, intermediate and immature).

In sheets 2 and 3 a measuring tape in centimeters has been added.

Of the commercial cultivars known to the inventor, the most similar in comparison to Akron is the cultivar Regal Davis, disclosed in U.S. Plant Pat. No. 8,292. Reference is made to attached Chart A, which compares certain characteristics of Akron to the same characteristics of Regal Davis.

Similar traits are capitulum form and type, ray floret color, and branching pattern. Akron has in general a larger diameter of capitulum than Regal Davis. The plant height of Akron and Regal Davis fall within the same range. However, Regal Davis requires one more growth regulator application to attain that plant height than Akron. Akron is 4 to 5 days faster in flowering response to short days than Regal Davis.

In the following description color references are made to The Royal Horticultural Society Colour Chart. The color values were determined on plant material grown as a pinched spray pot mum in Salinas, Calif. on Apr. 29, 1994.

Classification:

*Botanical.*—*Dendranthema grandiflora* cv Akron.

*Commercial.*—Daisy spray pot mum.

INFLORESCENCE

A. Capitulum:

*Form.*—Flat.

*Type.*—Daisy.

*Diameter across face.*—64 to 76 mm when fully opened.

B. Corolla of ray florets:

*Color (general tonality from a distance of three meters).*—Red-purple.

*Color (upper surface).*—71B.

*Color (under surface).*—70B.

*Shape.*—See photograph.

C. Corolla of disc florets:

*Color (mature).*—14B.

*Color (immature).*—144A.

D. Reproductive organs:

*Androecium.*—Present on disc florets only; moderate pollen.

*Gynoecium.*—Present on both ray and disc florets.

PLANT

A. General appearance:

*Height.*—18 to 30 cm when grown as a pinched pot mum with four cuttings in a 15 cm pot, and with 14 to 16 long days after direct sticking unrooted cuttings prior to start of short days and one applicaton of 2500 ppm B-9 SP.

*Branching pattern.*—Spreading and prolific, with 4 to 6 laterals after pinch.

B. Foliage:

*Color (upper surface).*—147A.

*Color (under surface).*—147B.

*Shape.*—See photograph.

CHART A

COMPARISON OF AKRON AND REGAL DAVIS

| CULTIVAR | AKRON | REGAL DAVIS |
|---|---|---|
| Ray floret color | Red-purple | Red-purple |
| Capitulum form and type | Flat daisy | Flat daisy |
| Diameter across face of capitulum | 64 to 76 mm | 64 to 70 mm |
| Flowering response | 50 to 56 days | 55 to 60 days |
| Plant height with 14 to 16 long days | 18 to 30 cm | 20 to 25 cm |
| Branching pattern | 4 to 6 laterals | 4 to 6 laterals |

COMPARISONS MADE OF PLANTS GROWN AS PINCHED SPRAY POT MUMS IN SALINAS, CALIFORNIA

I claim.

1. A new and distinct Chrysanthemum plant named Akron, as described and illustrated.

* * * * *

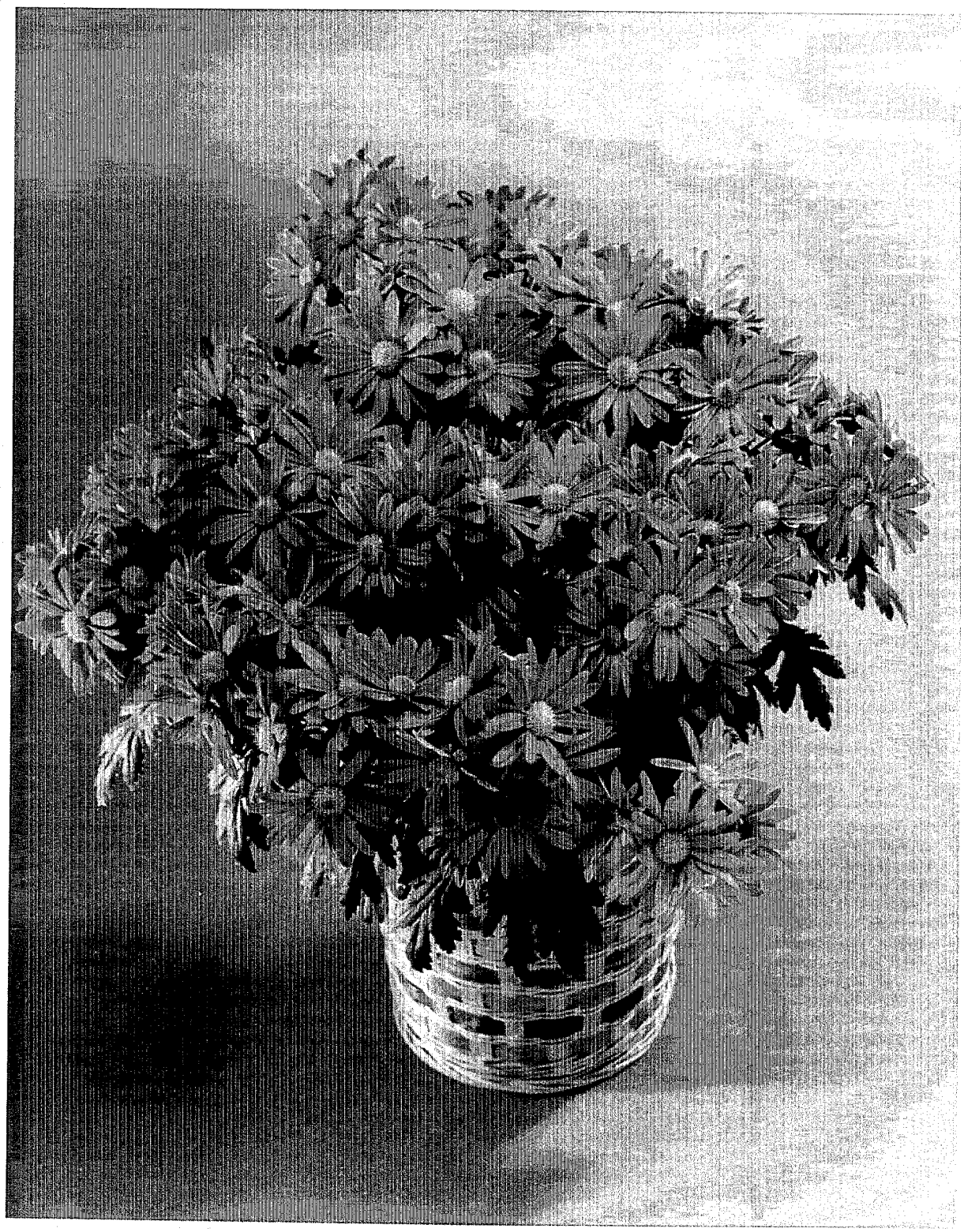

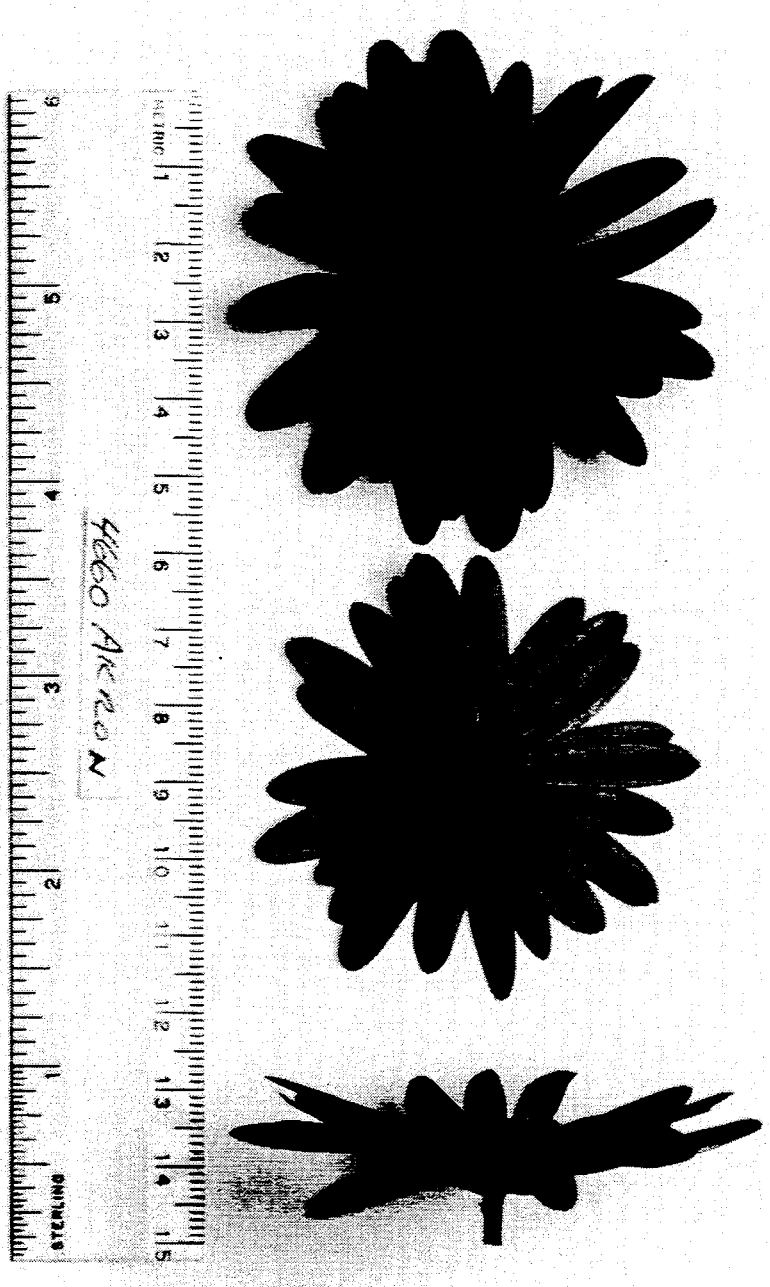
STERLING
4660 AKRON

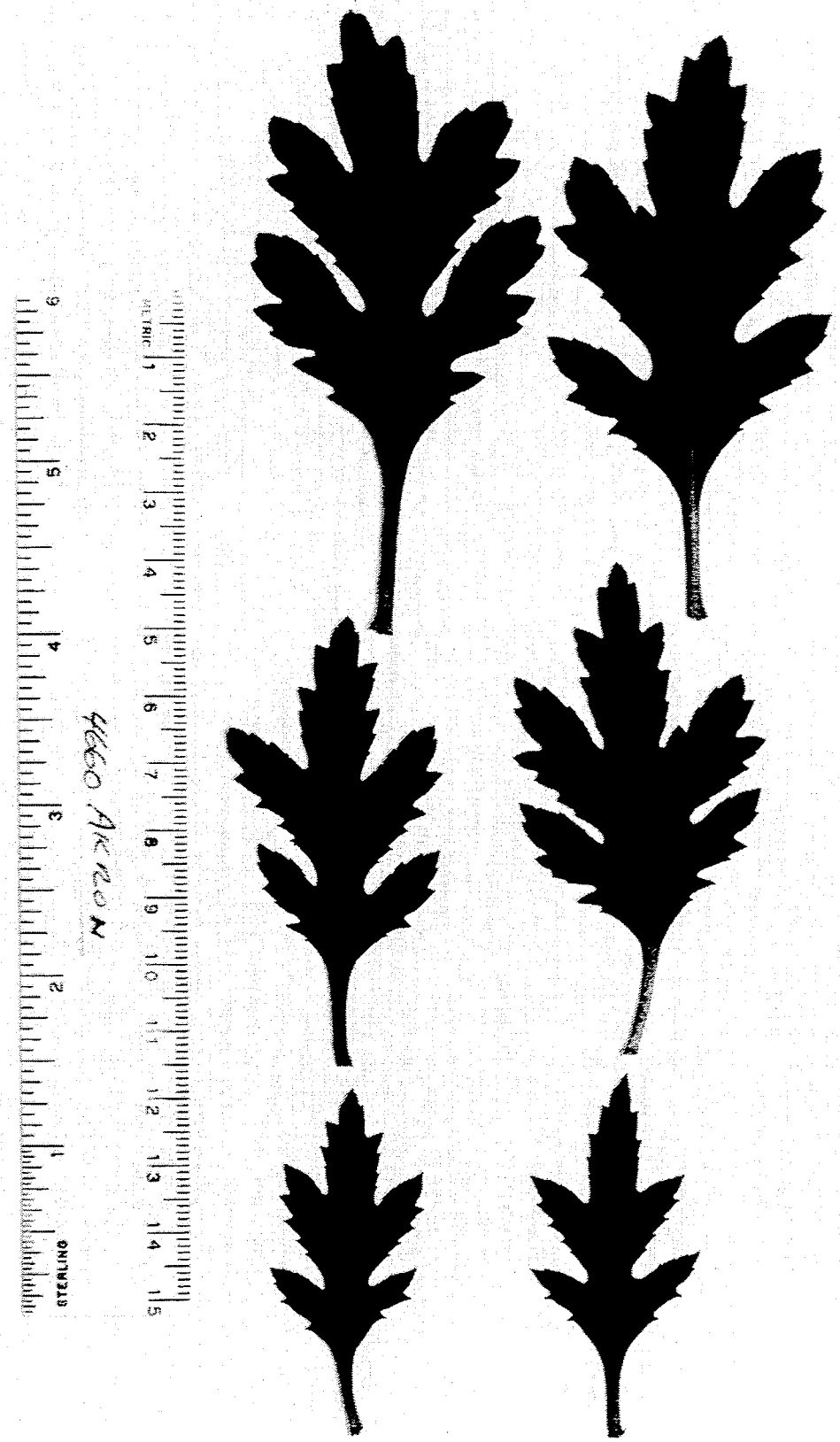
4660 AK120 N
METRIC
STERLING